US011878028B1

(12) United States Patent
Li et al.

(10) Patent No.: US 11,878,028 B1
(45) Date of Patent: *Jan. 23, 2024

(54) ANTI-TUMOR PHARMACEUTICAL COMPOSITION COMPRISING AZVUDINE

(71) Applicant: HENAN GENUINE BIOTECH CO., LTD., Pingdingshan (CN)

(72) Inventors: Pan Li, Pingdingshan (CN); Limin Jia, Pingdingshan (CN); Zhiyong Qin, Pingdingshan (CN); Zhaoyang Wang, Pingdingshan (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,402

(22) Filed: May 19, 2023

(30) Foreign Application Priority Data

Mar. 3, 2023 (CN) .......................... 202310201580.X

(51) Int. Cl.
*A61K 31/7068* (2006.01)
*A61P 35/00* (2006.01)
*A61K 31/506* (2006.01)

(52) U.S. Cl.
CPC ........ *A61K 31/7068* (2013.01); *A61K 31/506* (2013.01); *A61P 35/00* (2018.01)

(58) Field of Classification Search
CPC ................................................. A61K 31/7068
See application file for complete search history.

(56) References Cited

FOREIGN PATENT DOCUMENTS

WO WO 2020/206603 A1 10/2020

OTHER PUBLICATIONS

Abourehab et al, Globally Approved EGFR Inhibitors Insights into Their Synthesis, Target Kinases, Biological Activity, Receptor Interaction, and Metabolism, Molecules, 26(21):6677. (Year: 2021).*
Climent et al, Immunomodulatory Effects of Tyrosine Kinase Inhibitors to Illicit Cytotoxicity Against Cancer and Viral Infection, frontiers in Pharmacy, vol. 10, Article 1232. (Year: 2019).*
Extended European Search Report issued in European Patent Application No. 23174301.4, dated October 20, 2023.
Jing, X. et al., "FNC inhibits non-small cell lung cancer by activating the mitochondrial apoptosis pathway," *Genes & Genomics*, 44 (2022): 123-131.
Meng, Y. et al., "Discovery of Dosimertinib, a Highly Potent, Selective, and Orally Efficacious Deuterated EGFR Targeting Clinical Candidate for the Treatment of Non-Small-Cell Lung Cancer," *The Journal of Medicinal Chemistry*, 64 (2021): 925-937.

* cited by examiner

*Primary Examiner* — Carlos A Azpuru
(74) *Attorney, Agent, or Firm* — Parker Highlander PLLC

(57) ABSTRACT

The present invention discloses a pharmaceutical composition comprising azvudine and an EGFR/TKI inhibitor. The pharmaceutical composition of the present invention shows a good synergistic effect in antitumor, and can delay the generation of drug resistance and improve the therapeutic effect and safety, thereby achieving the goal of prolonging the survival of patients.

4 Claims, 4 Drawing Sheets

ANTI-TUMOR PHARMACEUTICAL COMPOSITION COMPRISING AZVUDINE

CROSS REFERENCE TO RELATED APPLICATIONS

This application claims the priority of Chinese Patent Application No. 202310201580.X, filed with the China National Intellectual Property Administration on Mar. 3, 2023, and titled with "ANTI-TUMOR PHARMACEUTICAL COMPOSITION COMPRISING AZVUDINE", which is hereby incorporated by reference in its entirety.

FIELD

The present invention belongs to the field of medicines, and in particular to an anti-tumor pharmaceutical composition comprising azvudine.

BACKGROUND

Deoxycytidine kinase (DCK) is an enzyme with broad substrate specificity, which can phosphorylate pyrimidine and purine deoxynucleosides, and is a key enzyme in the remedial pathway of deoxynucleotide biosynthesis. It is capable of maintaining normal DNA metabolism and phosphorylating a variety of antiviral and anticancer nucleoside analog drugs, which can only be activated after phosphorylation, thereby inhibiting tumor growth. In the past decades, apoptosis has been widely studied, and radiotherapy strategies targeting apoptosis have become one of the important means of tumor treatment.

Azvudine is a broad-spectrum RNA virus inhibitor. As a synthetic nucleoside analog of viral RNA-dependent RNA polymerase (RdRp), it is metabolized in cells into 5'-triphosphate metabolite (azvudine triphosphate) with antiviral activity, which can specifically act on the novel coronavirus polymerase (RdRp). It targets virus RdRp, and can block the synthesis and replication of RNA chain by inhibiting the activity of RdRp in the host cell. In July 2021, azvudine tablet was approved for marketing in China for the treatment of HIV-1 infected adult patients with high viral load. In July 2022, azvudine was approved for the treatment of novel coronavirus infection.

Patent document CN201010506595.X discloses use of azvudine in the treatment of tumors, such as colon cancer, liver cancer, gastric cancer, esophageal cancer, lung cancer, breast cancer, cervical cancer, leukemia, and lymphoma. It has been found that azvudine has significant inhibitory effect on various human cancer cells and transplanted tumors in animals.

EGFR (epidermal growth factor receptor) is a member of the transmembrane protein tyrosine kinase erbB receptor family. EGFR can form homodimers on the cell membrane by binding to its ligands, such as epidermal growth factor (EGF), or form heterodimers with other receptors in the family (such as erbB2, erbB3, or erbB4). The formation of these dimers can cause the phosphorylation of key tyrosine residues in EGFR cells, thereby activating multiple downstream signaling pathways in cells. These intracellular signaling pathways play important roles in cell proliferation, survival and anti-apoptosis. Dysregulation of EGFR signaling pathway, including increase in expression of ligands and receptors, and amplification and mutation of EGFR gene, can promote malignant transformation of cells and plays an important role in tumor cell proliferation, invasion, metastasis and angiogenesis. Overexpression of EGFR has been reported in many human malignant diseases, including bladder cancer, brain tumor, head and neck cancer, pancreatic cancer, lung cancer, breast cancer, ovarian cancer, colon cancer, prostate cancer and kidney cancer. In many cases, overexpression of EGFR is associated with poor prognosis of patients.

Lung cancer is one of the cancers with the highest incidence rate, and about 85% of lung cancer is non-small cell lung cancer (NSCLC). According to statistics, in 2020, there were 2.2 million new cases of lung cancer worldwide, and 1.8 million deaths from lung cancer, accounting for about 18% of cancer-related deaths, and the 5-year survival rate was only 10%-20%. According to statistics, about 10%-40% of NSCLC patients in different countries and regions around the world have epidermal growth factor receptor (EGFR) mutations. Therefore, targeting EGFR is an important treatment strategy for non-small cell lung cancer. Clinically, the use of EGFR inhibitors has become the standard therapy for the first-line treatment of EGFR mutation-positive non-small cell lung cancer.

The first-generation EGFR inhibitors are reversible competitive inhibitors, with representative drugs of gefitinib and erlotinib. However, 50-60% of patients developed acquired drug resistance after 1-2 years, and the main molecular mechanism is that the T790M mutation of EGFR leads to drug resistance. The second-generation EGFR inhibitors are covalent inhibitors, with a representative drug of afatinib, which are more effective than the first-generation EGFR inhibitors, but patients still developed drug resistance caused by T790M mutation. The third-generation EGFR inhibitors are mainly designed for the drug resistance caused by T790M mutation, with a representative drug of osimertinib. However, patients developed drug resistance caused by C797S mutation after about 1 year of use. At present, new EGFR inhibitors are being developed around the world to solve the drug resistance problem of EGFR inhibitors. China has a huge population base, a large number of smokers, and a higher incidence rate of lung cancer than other countries. Therefore, the development of new drugs for the treatment of lung cancer is of great significance to improve the 5-year survival rate of patients with lung cancer in China.

Multi-mechanism combination therapy is an important strategy to delay or even avoid the occurrence of tumor drug resistance. Based on the current treatment strategies for non-small cell lung cancer and the research progress of EGFR inhibitors, multi-mechanism combination drugs for non-small cell lung cancer can delay the occurrence of drug resistance, and improve efficacy and safety, thereby achieving the goal of prolonging the survival of patients.

SUMMARY

The present disclosure provides a pharmaceutical composition of azvudine and an EGFR inhibitor, and use of the pharmaceutical composition in the manufacture of a medicament for preventing or treating tumor diseases.

Compared with each single drug, the pharmaceutical composition of the present invention has the following advantages:
1. The combined administration improves the tumor-inhibiting effect of each single drug;
2. The occurrence of drug resistance is delayed, and the efficacy and safety are improved, thereby achieving the goal of prolonging the survival of patients.

In order to solve the technical problem of the present invention, the present invention provides a pharmaceutical composition, comprising:

(i) azvudine or a pharmaceutically acceptable salt, a stereoisomer or an isotopic derivative thereof;
(ii) an EGFR/TKI inhibitor.

In a preferred embodiment of the present invention, the EGFR/TKI inhibitor is selected from the group consisting of osimertinib, gefitinib, erlotinib, doxitinib, olmutinib, icotinib, pyrotinib, dacomitinib, afatinib, neratinib, lapatinib, ABT-414, varlitinib, HLX-07, tesevatinib, theliatinib, epaltinib succinate, S-222611, furmonertinib, befotertinib, rezivertinib, poziotinib and a combination thereof.

In a preferred embodiment of the present invention, the EGFR/TKI inhibitor is selected from the group consisting of osimertinib, doxitinib and a combination thereof.

In a preferred embodiment of the present invention, the (i) and (ii) are administered simultaneously, separately, or sequentially, or the (i) and (ii) exist in the same dosage form.

In addition, the present invention further provides the above pharmaceutical composition for use in treating a tumor-related disease.

In a preferred embodiment of the present invention, the tumor-related disease is selected from the group consisting of breast cancer, ovarian cancer, prostate cancer, melanoma, brain tumor, esophageal cancer, gastric cancer, liver cancer, pancreatic cancer, colorectal cancer, lung cancer, kidney cancer, skin cancer, glioblastoma, neuroblastoma, sarcoma, liposarcoma, osteochondroma, bone tumor, osteosarcoma, seminoma, testicular tumor, uterine cancer, head and neck tumor, multiple myeloma, malignant lymphoma, polycythemia vera, leukemia, thyroid tumor, ureter tumor, bladder tumor, gallbladder cancer, non-small cell lung cancer, cholangiocarcinoma and choriocarcinoma, preferably non-small cell lung cancer.

In some embodiments, the azvudine is administered at an amount selected from 1-100 mg, and the EGFR/TKI inhibitor is administered at an amount selected from 1-100 mg.

In the present disclosure, the azvudine is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg and 100 mg.

In the present disclosure, the EGFR/TKI inhibitor is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg and 100 mg.

In some embodiments, the azvudine is administered at an amount selected from 1-100 mg, and at a frequency of once a day, twice a day or three times a day, and the EGFR/TKI inhibitor is administered at an amount selected from 1-100 mg, and at a frequency of once a day, twice a day or three times a day.

In some embodiments, the azvudine is administered at an amount selected from 1-60 mg, and at a frequency of once a day or twice a day, and the EGFR/TKI inhibitor is administered at an amount selected from 1-60 mg, and at a frequency of once a day.

In some embodiments, the azvudine is administered at an amount selected from 1-20 mg, and at a frequency of once a day or twice a day, and the EGFR/TKI inhibitor is administered at an amount selected from 1-20 mg, and at a frequency of once a day.

In some embodiments, the azvudine is administered at an amount selected from 1-10 mg, and at a frequency of once a day or twice a day, and the EGFR/TKI inhibitor is administered at an amount selected from 1-10 mg, and at a frequency of once a day.

In some embodiments, the EGFR/TKI inhibitor is administered at an amount selected from the group consisting of 1 mg, 2 mg, 2.5 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg and 50 mg, and at a frequency of once a day or twice a day, and the EGFR/TKI inhibitor is administered at an amount selected from the group consisting of 10 mg, 20 mg, 40 mg and 60 mg, and at a frequency of once a day.

In some embodiments, the azvudine is administered at an amount selected from the group consisting of 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg and 20 mg, and at a frequency of once a day or twice a day, and the azvudine is administered at an amount selected from the group consisting of 1 mg, 2 mg, 4 mg and 6 mg, and at a frequency of once a day.

In some embodiments, the EGFR/TKI inhibitor is administered at an amount selected from the group consisting of 1 mg, 2 mg, 3 mg, 4 mg, 5 mg, 6 mg, 7 mg, 8 mg, 9 mg and 10 mg, and at a frequency of once a day or twice a day, and the EGFR/TKI inhibitor is administered at an amount selected from the group consisting of 10 mg, 20 mg, 40 mg and 60 mg, and at a frequency of once a day.

In some embodiments, the EGFR/TKI inhibitor is administered at an amount selected from the group consisting of 1 mg, 2 mg, 4 mg, 6 mg and 8 mg, and at a frequency of once a day or twice a day, and the EGFR/TKI inhibitor is administered at an amount selected from the group consisting of 1 mg, 2.5 mg, 5 mg and 10 mg, and at a frequency of once a day.

Route of the combined administration in the present invention is selected from the group consisting of oral administration, parenteral administration and transdermal administration, wherein the parenteral administration includes but is not limited to intravenous injection, subcutaneous injection and intramuscular injection, preferably oral administration.

The present invention further provides a pharmaceutical composition comprising the above azvudine and EGFR/TKI inhibitor and one or more pharmaceutically acceptable carriers, excipients and diluents. The pharmaceutical composition can be made into any pharmaceutically acceptable dosage form. For example, it can be formulated into a tablet, a capsule, a pill, a granule, a solution, a suspension, a syrup, an injection (including an injection solution, a sterile powder for injection and a concentrated solution for injection), a suppository, an inhalant or a spray. The pharmaceutical composition can also be made into the same dosage form, for example, the azvudine and EGFR/TKI inhibitor can be formulated into a composite tablet, a composite capsule, a composite pill, a composite granule, a composite solution, a composite suspension, a composite syrup, a composite injection (including an injection solution, a sterile powder for injection and a concentrated solution for injection), a composite suppository, a composite inhalant or a composite spray.

The present invention further provides a method for treating a tumor disease, comprising administering an effective amount of the above azvudine and an effective amount of the above EGFR/TKI inhibitor to a subject in need thereof.

The present invention further provides a pharmaceutical kit for use in a medicament for treating a tumor disease, which comprises the pharmaceutical composition of azvudine and EGFR/TKI inhibitor described in the present disclosure.

In the present invention, azvudine is administered in combination with an EGFR/TKI inhibitor, thereby enhancing the effect of drugs for treating a tumor disease.

The "combination" described in the present invention is a mode of administration that refers to the administration of at least one dose of azvudine and at least one dose of EGFR/TKI inhibitor within a certain period of time, wherein both substances show pharmacological effects. The period of time can be within one administration cycle, preferably within 4 weeks, within 3 weeks, within 2 weeks, within 1 week, or within 24 hours, more preferably within 12 hours. The azvudine and EGFR/TKI inhibitor can be administered simultaneously or sequentially. Such a treatment that azvudine and an EGFR/TKI inhibitor are administered by the same route of administration or by different routes of administration is included in this period of time.

DETAILED DESCRIPTION

Figure 1:
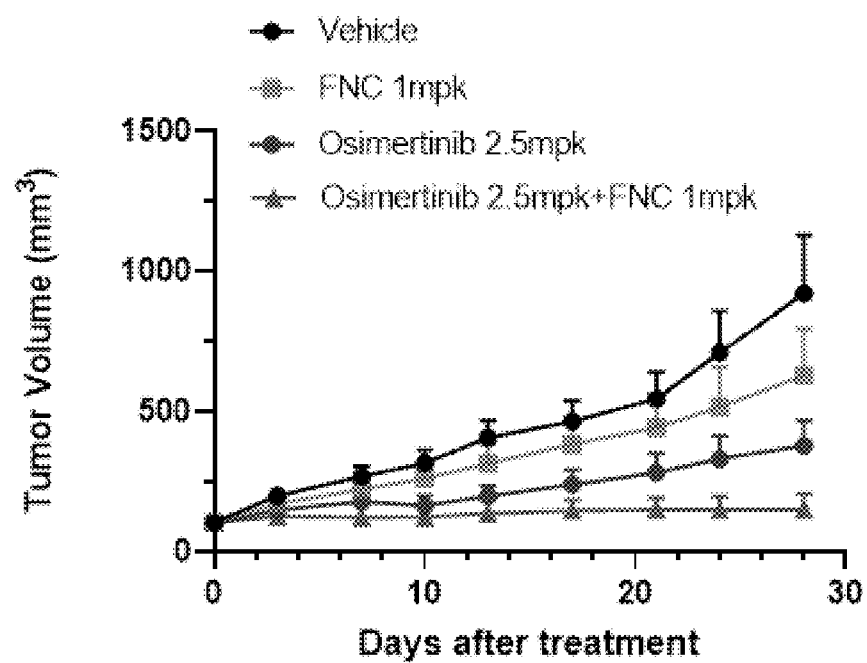
FIG. 1 shows the effects of FNC (wherein FNC is azvudine) and osimertinib used alone or in combination on the tumor volume of subcutaneously transplanted tumor in mice with human lung cancer NCI-H1975.

The following will describe the present disclosure in more detail in conjunction with examples, and the examples of the present disclosure are only used to illustrate the technical solutions of the present disclosure, and do not limit the essence and scope of the present disclosure.

Experimental materials
Experimental animals and breeding environment
Experimental animals
Species: Mice
Strain: BALB/c nude mice
Age and weight: 6-8 weeks old; 17.42-23.71 g
Gender: Female
Number: 40 (excluding the remaining mice after grouping)
Supplier: Zhejiang VitalRiver Experimental Animal Co., Ltd.
Breeding environment
The experiment was started after the animals arrived and kept in the experimental environment for 7 days. Animals were kept in IVC (independent ventilation system) cages (4 per cage) in SPF grade animal room. The number of animals in the cage, gender, strain, date of receipt, administration regimen, experiment number, group and date of start of the experiment were indicated on the animal information card for each cage. All cages, bedding and drinking water were sterilized before use. Cages, feed and drinking water were changed twice a week. The breeding environment and light conditions were as follows:
Temperature: 20~26° C.
Humidity: 40~70%
Lighting cycle: 12 hours of light, 12 hours of no light (the light was turned on at 8 am and turned off at 8 pm)
Cage: Cages were made of polycarbonate, with a volume of 325 mm×210 mm×180 mm. The bedding was corn cobs, and was changed twice a week.
Food: Experimental animals had free access to food (irradiation sterilized, dry pelleted food) throughout the whole experimental process.
Drinking water: Experimental animals can freely drink sterilized water.
Cage identification: The number of animals in the cage, gender, strain, date of receipt,
administration regimen, experiment number, group and date of start of the experiment should be indicated on the animal information card for each cage.
Animal identification: Experimental animals were identified with ear tags.

Example 1

Experimental purpose: To evaluate the anti-tumor effect of azvudine in combination with osimertinib in an animal model of BALB/c nude female mouse with subcutaneous xenograft of human lung cancer NCI-H1975 (EGFRL858R/T790M) cell line.

NCI-H1975 cells were cultured in RPMI 1640 medium containing 10% serum, at a constant temperature of 37° C. and 5% $CO_2$ under sterile condition. When the cell fusion degree of each bottle reached more than 90%, the cells were digested and resuspended in PBS. The cells were counted to reach a concentration of $5 \times 10^7$/ml by using a cell counter, and each mouse was injected with 0.1 ml of cell suspension. The $8^{th}$ generation cells were inoculated subcutaneously in nude mice. When the tumor grew to about 800 mm$^3$, the tumor was taken out and cut into a size of 2*2*2 mm$^3$. The chopped tumor was inoculated on the right back of each mouse. When the average volume of the tumor measured after inoculation reached 100-120 mm$^3$, grouping administration was started using a random stratified grouping method according to the tumor volume and animal body weight. The lung cancer cell line model was randomly divided into 4 experimental groups with 8 mice in each group. The mice were continuously administered for 28 days after grouping.

Tumor volume inhibition rate ($TGI_{TV}$):

$$TGI_{TV}(\%)=[1-(T_i-T_0)/(V_i-V_0)]\times 100\%$$

($T_i$: mean tumor volume of the treatment group on the $i^{th}$ day of administration, $T_0$: mean tumor volume of the treatment group on the $0^{th}$ day of administration; $V_i$: mean tumor volume of the solvent control group on the $i^{th}$ day of administration, $V_0$: mean tumor volume of the solvent control group on the $0^{th}$ day of administration)

Tumor weight suppression results ($T_{weight}/C_{weight}$):

At the end of the experiment, the surviving animals were euthanized, and the tumor tissue was taken, and weighed to obtain the tumor weight. The difference in tumor weights among each group was calculated to further calculate the tumor weight suppression result ($T_{weight}/C_{weight}$) according to the following formula:

Tumor weight suppression result($T_{weight}/C_{weight}$)%=$W_{Mean\ treatment\ group}/W_{Mean\ solvent\ control\ group}\times 100\%$, where $W$ refers to tumor weight.

Tumor Volume Suppression Results

The curves of tumor volume changes in tumor-bearing mice in each group are shown in FIG. 1, and the average tumor volume and significance statistics at different time points are shown in Table 1. The day of the first administration was recorded as Day0. After 28 days of administration, compared with the control group, except for G2, the tumor volume of each administration group showed a significant difference. The groups were sorted according to tumor TGI as follows: osimertinib+azvudine (2.5+1 mpk) group (94.5%)>osimertinib group (66.4%)>azvudine (1 mpk) group (35.7%).

TABLE 1

Effects of the test drugs on tumor volume in tumor-bearing mice

| Group | Test substance | Tumor volume (mm³)$^a$ | | $TGI_{TV}$ (%) | $P^b$ |
|---|---|---|---|---|---|
| | | On the $0^{th}$ day of administration | On the $28^{th}$ day of grouping administration | | |
| G1 | Vehicle | 104.5 ± 3.3 | 920.4 ± 209.1 | — | — |
| G2 | Azvudine (1 mpk) | 104.0 ± 3.0 | 628.3 ± 165.4 | 35.7% | 0.292 |
| G3 | Osimertinib (2.5 mpk) | 103.5 ± 2.5 | 377.9 ± 90.8 | 66.4% | 0.032* |
| G4 | Osimertinib + Azvudine (2.5 + 1 mpk) | 103.8 ± 2.6 | 148.9 ± 57.8 | 94.5% | 0.003*** |

Note:
$^a$mean ± standard error;
$^b$Statistical comparison between the tumor volume of the administration group and the tumor volume of the control group on the $28^{th}$ day of grouping administration by T-test analysis, where *p < 0.05, p < 0.01, *P < 0.005.

Tumor Weight Suppression Results

Figure 2:
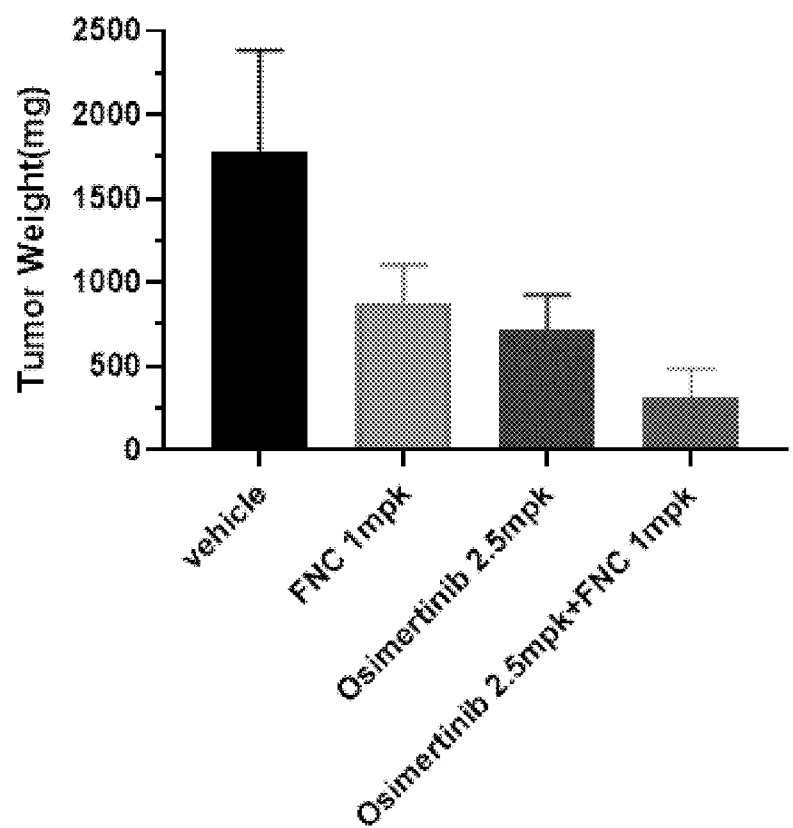
FIG. 2 shows the effects of azvudine and osimertinib used alone or in combination on tumor weight in mice.

The $T_{weight}/C_{weight}$ percentages of the tumor-bearing mice in the control group and the treatment group are shown in Table 2, and the curves of tumor weight changes in the tumor-bearing mice in each group are shown in FIG. 2.

TABLE 2

$T_{weight}/C_{weight}$ of tumor weight in mice administered with test drugs

| Group | Test drug | Tumor weight (mg)$^a$ | $T_{weight}/C_{weight}$ (%) | $P^b$ |
|---|---|---|---|---|
| G1 | Vehicle | 1777.6 ± 607.6 | — | — |
| G2 | Azvudine (1 mpk) | 879.3 ± 226.9 | 49.5% | 0.188 |
| G3 | Osimertinib (2.5 mpk) | 716.9 ± 207.4 | 40.3% | 0.121 |
| G4 | Osimertinib + Azvudine (1 mpk) | 315.9 ± 171.1 | 17.8% | 0.36 |

Note:
$^a$mean ± standard error.
$^b$Statistical comparison of the tumor weight between the drug treatment group and the control group at the end point of the experiment by T-test analysis, where *p < 0.05, p < 0.01, *P < 0.005.

The tumor inhibition rate TGI (%) was statistically analyzed, and the results show that in the lung cancer cell line NCI-H1975 tumor-bearing mouse model, azvudine had an inhibitory effect on tumor proliferation in a dose-dependent manner. The combined administration of azvudine and osimertinib improved the tumor inhibitory effect of each single drug. The administration amount of the drug to be tested in this experiment did not produce obvious toxic and side effects on animals, showing good safety.

Example 2

Experimental purpose: To evaluate the anti-tumor effect of azvudine in combination with doxitinib in an animal model of BALB/c nude female mouse with subcutaneous xenograft of human lung cancer NCI-H1975 (EGFRL858R/T790M) cell line.

NCI-H1975 cells were cultured in RPMI 1640 medium containing 10% fetal bovine serum in a 37° C. and 5% $CO_2$ incubator. The cells were routinely passaged once a week. When the cell saturation reached 80%-90% and the number achieved the requirement, the cells were collected, counted and inoculated.

Tumor Cell Inoculation 0.1 mL (5×10⁶) of NCI-H1975 cells were subcutaneously inoculated on the right back of each mouse, and the grouping administration was started when the average tumor volume reached about 154 mm 3.

The experimental index was to investigate whether tumor growth was inhibited, delayed or cured. Tumor diameter was measured with a vernier caliper twice a week or every other day. The tumor volume was calculated according to the formula of: $V=0.5a\times b^2$, where a and b represented the long diameter and short diameter of the tumor, respectively.

The anti-tumor efficacy of the compounds was evaluated by TGI (%) or relative tumor proliferation rate T/C (%). TGI (%) reflected the inhibition rate of tumor growth. TGI (%) was calculated according to the formula of: TGI (%)=[1-(average tumor volume at the end of administration of a certain treatment group−average tumor volume at the beginning of administration of this treatment group)/(average tumor volume at the end of treatment of solvent control group−average tumor volume at the beginning of treatment of the solvent control group)]×100%.

Relative tumor proliferation rate T/C (%) was calculated according to the formula as follows: T/C %=$T_{RTV}$/$C_{RTV}$×100% ($T_{RTV}$ represented the average RTV of the treatment group; $C_{RTV}$ Represented the Average RTV of the Negative Control Group). Relative Tumor Volume (RTV) was calculated based on the results of measurement of tumor according to the formula of RTV=$V_t$/$V_0$, where $V_0$ represented the tumor volume measured during grouping administration (i.e. $d_0$), and $V_t$ represented the tumor volume obtained in a certain measurement, and $T_{RTV}$ and $C_{RTV}$ were collected from the data on the same day.

Statistical Analysis

Statistical analysis included mean and standard error (SEM) of tumor volume at each time point for each group (see Table 3 for specific data). The treatment group showed the best treatment effect on the 20$^{th}$ day after administration at the end of the experiment, and the statistical analysis was performed based on this data to evaluate the differences between the groups. The comparison between two groups was analyzed by T-test, and the comparison between three or more groups was analyzed by one-way ANOVA. All data analysis was performed with Prism. p<0.05 was considered significant difference.

Figure 3:
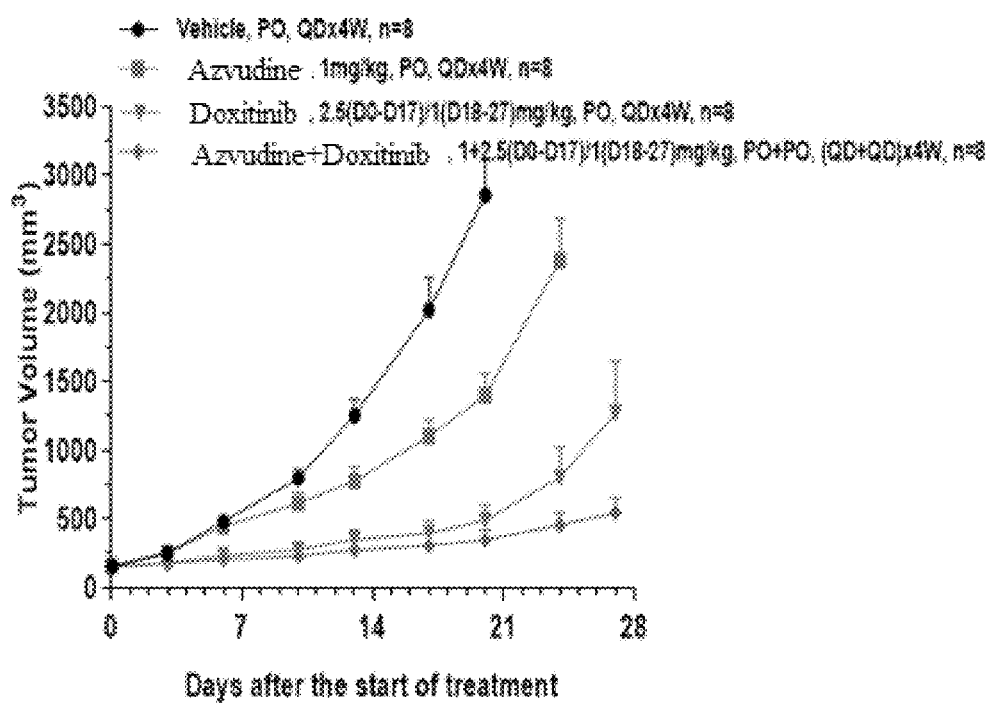
FIG. 3 shows the effects of azvudine and doxitinib used alone or in combination on the tumor volume of subcutaneously transplanted tumor in mice with human lung cancer NCI-H1975.

The tumor volume changes in each group after treatment of test drugs on BALB/c nude mice with subcutaneous xenograft of tumor of NCI-H1975 cell are shown in FIG. 3, and the curves of tumor volume changes in tumor-bearing mice in each group are shown in FIG. 3.

TABLE 3

Tumor volume in each group at different time points

|   | Vehicle | Azvudine 1 mg/kg | Doxitinib 2.5 mg/kg | Azvudine + Doxitinib 1 + 2.5 mg/kg |
|---|---|---|---|---|
| 0 | 154 ± 9 | 154 ± 11 | 154 ± 12 | 154 ± 12 |
| 3 | 253 ± 15 | 252 ± 25 | 180 ± 19 | 176 ± 13 |
| 6 | 481 ± 44 | 447 ± 46 | 232 ± 27 | 206 ± 22 |
| 10 | 795 ± 63 | 614 ± 78 | 277 ± 34 | 231 ± 28 |
| 13 | 1,253 ± 117 | 774 ± 106 | 350 ± 65 | 274 ± 45 |
| 17 | 2,019 ± 238 | 1,102 ± 118 | 395 ± 86 | 308 ± 53 |
| 20 | 2,854 ± 261 | 1,396 ± 162 | 492 ± 109 | 348 ± 69 |

TABLE 3-continued

Tumor volume in each group at different time points

|   | Vehicle | Azvudine 1 mg/kg | Doxitinib 2.5 mg/kg | Azvudine + Doxitinib 1 + 2.5 mg/kg |
|---|---|---|---|---|
| 24 | — | 2,382 ± 305 | 802 ± 220 | 456 ± 87 |
| 27 | — | — | 1,272 ± 374 | 544 ± 109 |

Note:
a. Mean ± SEM
b. Days after administration

Index for evaluation on anti-tumor drug efficacy

TABLE 4

Evaluation of anti-tumor effect of the test drugs on the NCI-H1975 cell xenograft tumor model (calculated based on the tumor volume on the 20$^{th}$ day after administration)

| Treatment | Tumor volume (mm3)$^a$ on the 20$^{th}$ day | T/C (%) | TGI$^b$ (%) | p value (%) |
|---|---|---|---|---|
| Vehicle | 2,854 ± 261 | — | — | — |
| Azvudine (1 mg/kg) | 1,396 ± 162 | 47.02 | 54.01 | <0.0001 |
| Doxitinib (2.5 mg/kg) | 492 ± 109 | 15.77 | 87.50 | <0.0001 |
| Azvudine + Doxitinib (1 + 2.5 mg/kg) | 348 ± 69 | 11.42 | 92.82 | <0.0001 |

Note:
$^a$Mean ± SEM;
$^b$TGI was calculated according to TGI (%) = [1 − ($T_{20}$ − $T_0$)/($V_{20}$ − $V_0$)] × 100.

Figure 4:
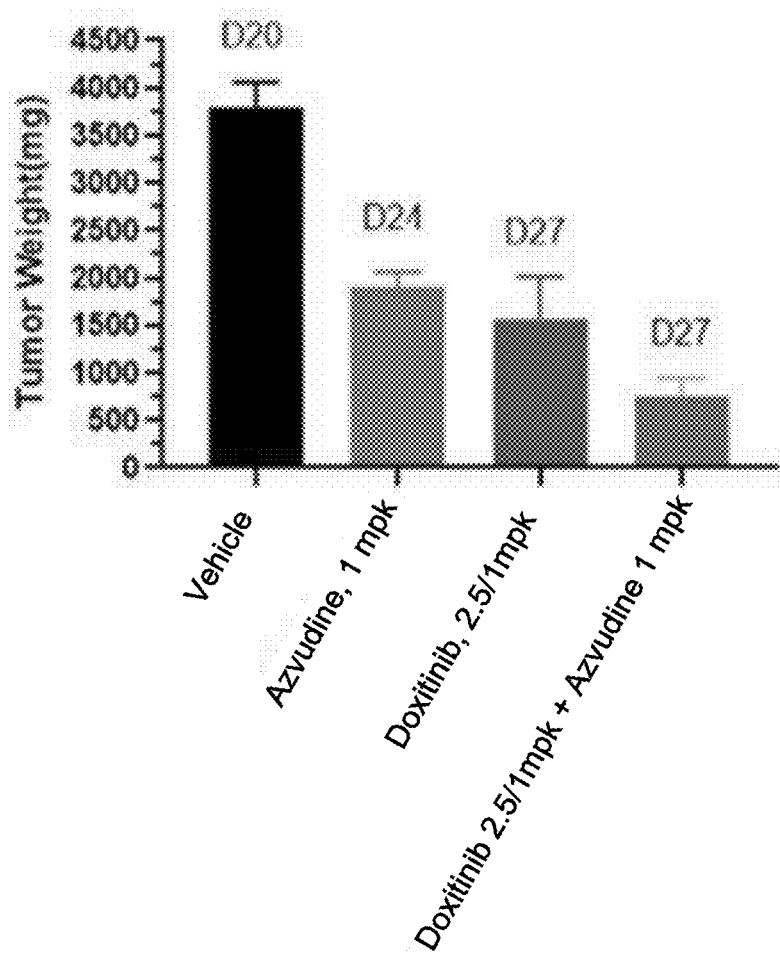
FIG. 4 shows the effects of azvudine and doxitinib used alone or in combination on tumor weight in mice.
Figure 5:
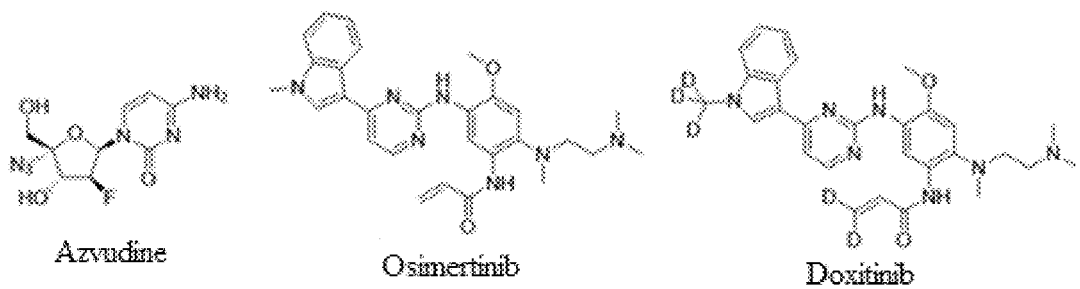
FIG. 5 shows the chemical structures of azvudine, osimertinib, and doxitinib.

The curves of tumor weight changes in tumor-bearing mice in each group are shown in FIG. 4.

Test Results

The experiment shows that in the human lung cancer cell line NCI-H1975 xenograft tumor mouse model, azvudine had inhibitory effect on tumor growth in a dose-dependent manner. The combined administration of azvudine and doxitinib improved the tumor-inhibiting effect of each single drug.

Although the specific embodiments of the present invention have been described above, those skilled in the art should understand that these are only examples, and various changes or modifications can be made to these embodiments without departing from the principle and essence of the present invention. Accordingly, the protection scope of the present invention is defined by the claims.

The invention claimed is:

1. A pharmaceutical composition, comprising:
   (i) azvudine or a pharmaceutically acceptable salt, or a stereoisomer thereof;
   (ii) an EGFR/TKI inhibitor.

2. The pharmaceutical composition according to claim 1, wherein, the EGFR/TKI inhibitor is selected from the group consisting of osimertinib, gefitinib, erlotinib, doxitinib, olmutinib, icotinib, pyrotinib, dacomitinib, afatinib, neratinib, lapatinib, ABT-414, varlitinib, HLX-07, tesevatinib, theliatinib, epaltinib succinate, S-222611, furmonertinib, befotertinib, rezivertinib, poziotinib and a combination thereof.

3. The pharmaceutical composition according to claim 1, wherein the EGFR/TKI inhibitor is selected from the group consisting of osimertinib, doxitinib and a combination thereof.

4. The pharmaceutical composition according to claim 1, wherein the (i) and (ii) are administered simultaneously, separately, or sequentially, or the (i) and (ii) exist in the same dosage form.

* * * * *